United States Patent
Foti, Jr. et al.

(10) Patent No.: US 11,170,895 B2
(45) Date of Patent: Nov. 9, 2021

(54) OLFACTORY COGNITIVE DIAGNOSIS

(71) Applicant: International Business Machines Corporation, Armonk, NY (US)

(72) Inventors: Joseph Foti, Jr., New Windsor, NY (US); Elisabeth R. Stahl, Shaker Heights, OH (US); Clarisse T. Taafe-Hedglin, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 758 days.

(21) Appl. No.: 15/634,010

(22) Filed: Jun. 27, 2017

(65) Prior Publication Data

US 2018/0373840 A1   Dec. 27, 2018

(51) Int. Cl.
  *G16H 50/20* (2018.01)
  *G16H 10/20* (2018.01)
  (Continued)

(52) U.S. Cl.
  CPC ............. *G16H 50/20* (2018.01); *G16H 10/20* (2018.01); *G16H 10/60* (2018.01); *G16H 20/70* (2018.01)

(58) Field of Classification Search
  CPC ........ G16H 50/20; G16H 10/60; G16H 10/20; G16H 10/30; G16H 10/32; G16H 10/34;
  (Continued)

(56) References Cited

U.S. PATENT DOCUMENTS 8,275,803 B2   9/2012  Brown et al.
2003/0008407 A1 *   1/2003  Fu .......................... A61B 5/082
                                                                    436/161
(Continued)

FOREIGN PATENT DOCUMENTS

WO    WO-2015028364 A1 *   3/2015  ............. G16H 40/67

OTHER PUBLICATIONS

High, Rob, "The Era of Cognitive Systems: An Inside Look at IBM Watson and How it Works", IBM Corporation, Redbooks, Dec. 12, 2012, 16 pages.

(Continued)

*Primary Examiner* — Jonathan Ng
*Assistant Examiner* — Christopher B Wehrly
(74) *Attorney, Agent, or Firm* — Stephen J. Walder, Jr.; Margaret McNamara

(57) ABSTRACT

An olfactory-based cognitive system is implemented by receiving a request from a user, the request including one or more attributes, wherein the one or more attributes include at least olfactory-sensed data and an identification of the olfactometer or electronic nose utilized to gather the olfactory-sensed data. A set of candidate recommendations is generated utilizing the one or more attributes from data sources. A confidence score is generated for each candidate recommendation in the set of candidate recommendations indicating a confidence that the corresponding candidate recommendation is valid to address the request. Each candidate recommendation in the set of candidate recommendations is ranked according to its respective confidence scores. The ranked listing of candidate recommendations is presented to the user for use in addressing the request.

14 Claims, 6 Drawing Sheets

(51) Int. Cl.
*G16H 10/60* (2018.01)
*G16H 20/70* (2018.01)

(58) Field of Classification Search
CPC ........ G16H 20/70; G06Q 50/22; G06Q 50/24; G06F 19/30; G06F 19/32; G06F 19/34; G06F 19/3456; G06F 19/3462; G06F 19/3468; G06F 19/3475; G06F 19/3481
USPC .......................................................... 705/2
See application file for complete search history.

(56) References Cited

U.S. PATENT DOCUMENTS

| | | |
|---|---|---|
| 2007/0077204 A1 | 4/2007 | Devanand et al. |
| 2009/0287678 A1 | 11/2009 | Brown et al. |
| 2011/0066587 A1 | 3/2011 | Ferrucci et al. |
| 2011/0071850 A1* | 3/2011 | Nuthi .................... G06Q 50/22 705/3 |
| 2011/0125734 A1 | 5/2011 | Duboue et al. |
| 2013/0007055 A1 | 1/2013 | Brown et al. |
| 2013/0018652 A1 | 1/2013 | Ferrucci et al. |
| 2013/0066886 A1 | 3/2013 | Bagchi et al. |
| 2015/0112161 A1 | 4/2015 | Mills |
| 2016/0091470 A1* | 3/2016 | Gafsou .............. G01N 33/0001 73/23.34 |
| 2016/0287161 A1 | 10/2016 | Smith et al. |

OTHER PUBLICATIONS

McCord, M.C. et al., "Deep parsing in Watson", IBM J. Res, & Dev. vol. 56 No. 3/4 Paper 3, May/Jul. 2012, pp. 3:1-3:15.

Yuan, Michael J., "Watson and healthcare, How natural language processing and semantic search could revolutionize clinical decision support", IBM Corporation, IBM developerWorks, http://www.ibm.corn/developerworks/industry/library/ind-watsoni, Apr. 12, 2011, 14 pages.

* cited by examiner

OLFACTORY COGNITIVE DIAGNOSIS

BACKGROUND

The present application relates generally to an improved data processing apparatus and method and more specifically to mechanisms for olfactory cognitive diagnosis.

With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating Question and Answer (QA) systems which may take an input question, analyze it, and return results indicative of the most probable answer to the input question. QA systems provide automated mechanisms for searching through large sets of sources of content, e.g., electronic documents, and analyze them with regard to an input question to determine an answer to the question and a confidence measure as to how accurate an answer is for answering the input question.

Examples, of QA systems are Siri® from Apple®, Cortana® from Microsoft®, and question answering pipeline of the IBM Watson™ cognitive system available from International Business Machines (IBM®) Corporation of Armonk, N.Y. The IBM Watson™ system is an application of advanced natural language processing, information retrieval, knowledge representation and reasoning, and machine learning technologies to the field of open domain question answering. The IBM Watson™ system is built on IBM's DeepQA™ technology used for hypothesis generation, massive evidence gathering, analysis, and scoring. DeepQA™ takes an input question, analyzes it, decomposes the question into constituent parts, generates one or more hypothesis based on the decomposed question and results of a primary search of answer sources, performs hypothesis and evidence scoring based on a retrieval of evidence from evidence sources, performs synthesis of the one or more hypothesis, and based on trained models, performs a final merging and ranking to output an answer to the input question along with a confidence measure.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system comprising at least one processor and at least one memory is provided. The at least one memory comprising instructions executed by the at least one processor to cause the at least one processor to implement an olfactory-based cognitive system. The olfactory-based cognitive system operates to receive a request from a user, the request including one or more attributes, wherein the one or more attributes include at least olfactory-sensed data and an identification of the olfactometer or electronic nose utilized to gather the olfactory-sensed data. The olfactory-based cognitive system operates to receive generate a set of candidate recommendations utilizing the one or more attributes from data sources. The olfactory-based cognitive system operates to receive generate a confidence score for each candidate recommendation in the set of candidate recommendations indicating a confidence that the corresponding candidate recommendation is valid to address the request. The olfactory-based cognitive system operates to receive rank each candidate recommendation in the set of candidate recommendations according to its respective confidence scores. The olfactory-based cognitive system operates to receive present a ranked listing of candidate recommendations to the user for use in addressing the request.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
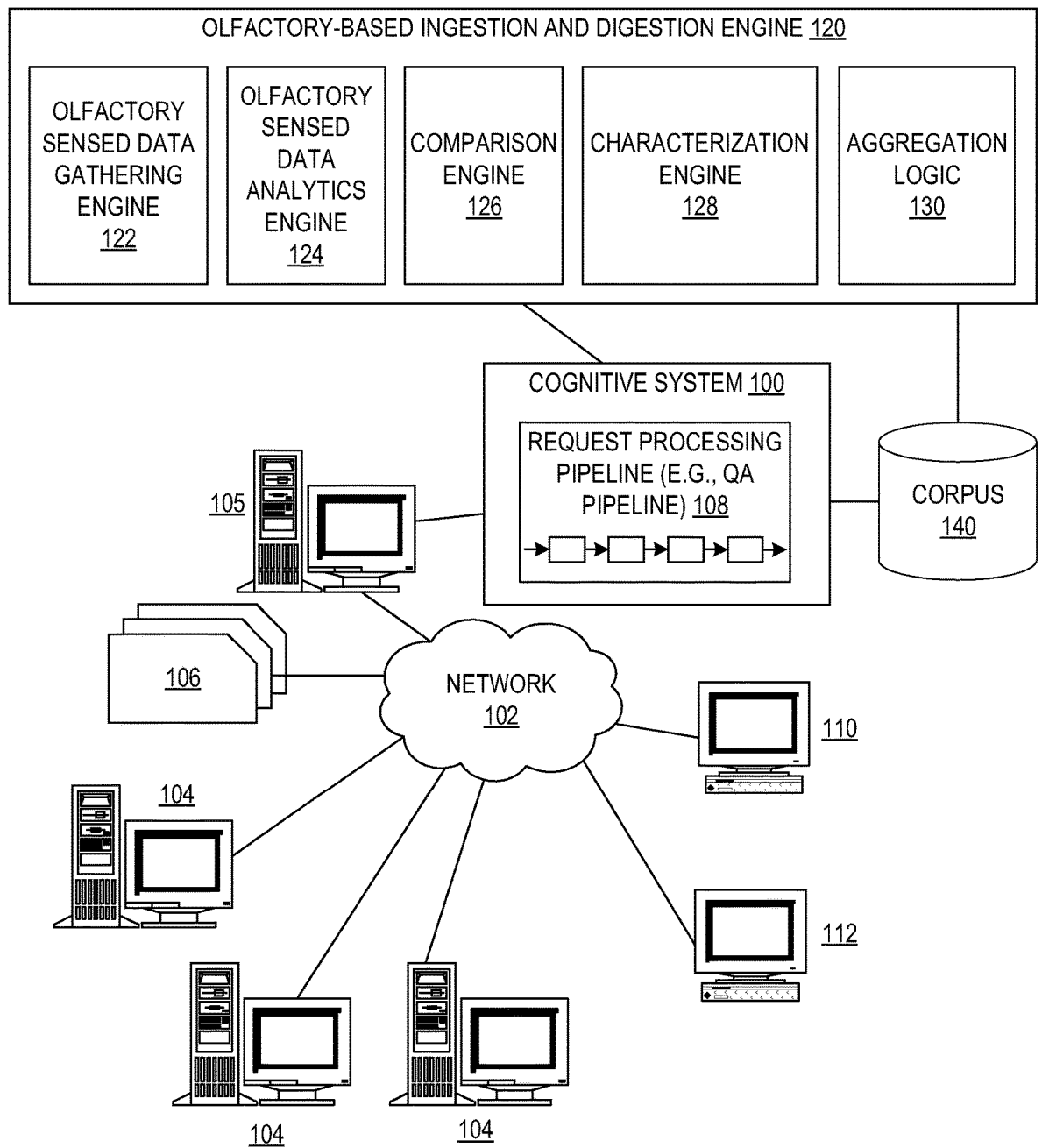
FIG. 1 depicts a schematic diagram of one illustrative embodiment of a cognitive system in a computer network.

Cognitive computing is the simulation of human thought processes in a computerized model. Cognitive computing involves self-learning systems that use data mining, pattern recognition, and natural language processing to mimic the way the human brain works and has already proven useful for numerous applications. Cognitive computing relies on components used to develop and behaviors resulting from systems that learn at scale, reason with purpose, and interact with humans naturally. Features of cognitive systems may include:

Adaptive: The cognitive systems may learn as information changes and as goals and requirements evolve. The cognitive systems may resolve ambiguity and tolerate unpredictability. The cognitive systems may be engineered to feed on dynamic data in real time or near real time.

Interactive: The cognitive systems may interact easily with users so that those users may define their needs comfortably. The cognitive systems may also interact with other processors, devices, Cloud services, or the like, as well as with people.

Iterative and stateful: The cognitive systems may aid in defining a problem by asking questions or finding additional source input if a problem statement is ambiguous or incomplete. The cognitive systems may "remember" previous interactions in a process and return information that is suitable for the specific application at that point in time.

Contextual: The cognitive systems may understand, identify, and extract contextual elements such as meaning, syntax, time, location, appropriate domain, regulations, user's profile, process, task, goal or the like. The cognitive systems may draw on multiple sources of information, including both structured and unstructured digital information, as well as sensory inputs (visual, gestural, auditory, or sensor-provided).

Multitudes of organizations are seeing the need to pursue cognitive computing models (i.e. speech recognition, sentiment analysis, facial recognition, medical diagnosis, etc.) across many industries including Healthcare, Manufacturing, Financial, Transportation, Retail, etc.

All cognitive systems require a large corpus of data, usually unstructured textual data, upon which to apply various analytics techniques. After ingesting a corpus of knowledge, which is then curated by experts on any given subject, cognitive systems are trained by being fed a series of question-and-answer pairs. This machine "knowledge" is then enhanced as humans interact with the system, providing feedback on the accuracy of the system's responses. Everyday 2.5 quintillion bytes of new data are produced—the majority of which is unstructured. While this data holds many possibilities, the data is vastly underutilized because of the complexity and challenges in using this data. In fact, typical organizations only leverage 8% of this data.

One of the most well-known capabilities of cognitive systems involves ingesting and digesting a corpus, i.e. a body of textual knowledge, from which the cognitive systems learn to make inferences. In areas where there is a well-established body of written knowledge, ingesting and digesting a corpus may be straightforward. But challenges arise when the needed knowledge fails to be in the corpus. As an example, some drug remedies are not in the literature yet. Further, definitions of cancer and cancer variations are being redefined all the time as the biological characteristics of each one are further understood. That is, science is changing more rapidly than the published literature. So it is not just a matter of feeding the cognitive systems some text. Organizations have had to employ human experts to create many question/answer pairs and incorporate "expert recommendations" to address this gap between the speed knowledge advances and the time it takes to be codified into online guidelines.

Cognitive computing platforms encompass machine learning, reasoning, natural language processing, speech and vision, human-computer interaction, dialog, narrative generation. Of the five senses that exist, there is one sense that is not yet addressed by cognitive systems but is imperative for many organizational uses—olfaction. That is, current computer-based systems do not utilize olfactory-sensed data in providing cognitive-based diagnoses.

Therefore, the illustrative embodiments provide a computer-based solution where mechanisms within a cognitive system provide olfactory-based cognitive diagnosis. Olfaction is mediated by specialized sensory cells of the nasal cavity of vertebrates, which may be considered analogous to sensory cells of the antennae of invertebrates. In humans, olfaction occurs when odorant molecules bind to specific sites on the olfactory receptors. These receptors are used to detect the presence of smell. The receptors come together at the glomerulus, a structure which transmits signals to the olfactory bulb, a brain structure directly above the nasal cavity and below the frontal lobe. The mechanisms of the illustrative embodiment provide a cognitive system that utilizes olfaction to detect, for example, medical diseases, automotive issues, or the like. The Internet of Things (IoT) component involves an olfactometer or an electronic nose. An olfactometer is an instrument used to detect and measure odor. Olfactometers are used in conjunction with human subjects in laboratory settings, most often in market research, to quantify and qualify human olfaction. An electronic nose is a device that identifies the specific components of an odor and analyzes its chemical makeup to identify the odor. An electronic nose consists of a mechanism for chemical detection, such as an array of electronic sensors, and a mechanism for pattern recognition, such as a neural network. Examples of these olfactometers or electronic noses may include:

1. Caltech electronic nose: Individual sensor film responds to a variety of vapors. Chemicals will partition into the polymer and cause it to swell to varying degrees. An array of sensors, containing different polymers, yields a distinct fingerprint for each odor because the swelling properties over the entire array are different for different vapors. The pattern of resistance changes on the array is diagnostic of the vapor, while the amplitude of the patterns indicates the concentration of the vapor.

2. Mass-spectrometer: Systems based on a mass-spectrometer in combination with pattern recognition are sometimes presented as an 'electronic nose' application or 'artificial olfaction.'

3. Quartz Microbalance (QMB): A quartz crystal with a chemically active surface, usually a polymer. When gas molecules adsorb to the surface, the mass changes and the resonant frequency of the crystal shifts.

4. Micro hotplate Metal-oxide sensor (MOS): Certain metal-oxides behave as semiconductors at higher temperatures. Sensors based on this are designed as having a heater element and a sensor element (sintered metal-oxide with or without catalyst). Both elements are separated by a very thin isolating membrane. Redox-reactions occurring at the sensor surface result in changes in resistance which can be measured.

The mechanisms of the illustrative embodiments ingest and digest olfactometer or electronic nose data to coincide with other data in the corpus of the cognitive system thereby improving the learning and diagnostics provided by the cognitive systems. However, different electronic noses and olfactometers may need to be applied, leveraged, or the like, so that the information within the corpus may be cross-analyzed for a full range of analysis.

In order to improve the diagnostics provide by the cognitive system using olfaction, for each sensed odor in a plurality of sensed odors sensed by a plurality of electronic noses and olfactometers, the mechanisms of the illustrative embodiments gather olfactory-sensory data Obtained via the plurality of electronic noses and olfactometers; load the olfactory-sensory data as an odor profile into the corpus; analyze and create insight on olfactory-sensory data from the plurality of electronic noses and olfactometers through composite scoring of the olfactory-sensory data associated with the odor; add the assessment value data associated with the odor to the corpus; compare cognitive diagnosis with actual olfactory-sensory data; characterize the odor based on measurements; and repeat the process until all olfactory-sensory data is collected and characterized.

Then, with the characterized olfactory-sensed data being available within the corpus, when a question is submitted to the cognitive system, the cognitive system utilized the characterized olfactory-sensed data to improve the accuracy of diagnostics provide by the cognitive system in providing a set of answers to the question. For example, if a question is submitted to the cognitive system regarding basal cell carcinoma, i.e. skin cancer, along with olfactory-sensory data, the cognitive system may utilize odor profiles associated with different types of basal cell carcinomas to provide additional insight and diagnosis, there by identifying the basal cell carcinoma as cystic basal cell carcinoma, cicatricial basal cell carcinoma, or another type. Thus, using the characterized olfactory-sensed data, the cognitive system outputs a ranked set of answers to meet client goals based on cognitive findings.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for providing a cognitive diagnosis using characterized olfactory-sensed data. The mechanisms of the illustrative embodiments ingest and digest olfactometer or electronic nose data to coincide with other data in the corpus of the cognitive system thereby improving the learning and diagnostics provided by the cognitive systems. For each sensed odor in a plurality of sensed odors sensed by a plurality of electronic noses and olfactometers, the mechanisms of the illustrative embodiments gather olfactory-sensory data obtained via the plurality of electronic noses and olfactometers; load the olfactory-sensory data as an odor profile into the corpus; analyze and create insight on olfactory-sensory data from the plurality of electronic noses and olfactometers through composite scoring of the olfactory-sensory data associated with the odor; add the assessment value data associated with the odor to the corpus; compare cognitive diagnosis with actual olfactory-sensory data; characterize the odor based on measurements; and repeat the process until all olfactory-sensory data is collected and characterized. Then, with the characterized olfactory-sensed data being available within the corpus, when a question is submitted to the cognitive system, the cognitive system utilized the characterized olfactory-sensed data to improve the accuracy of diagnostics provide by the cognitive system in providing a set of answers to the question.

Figure 2:
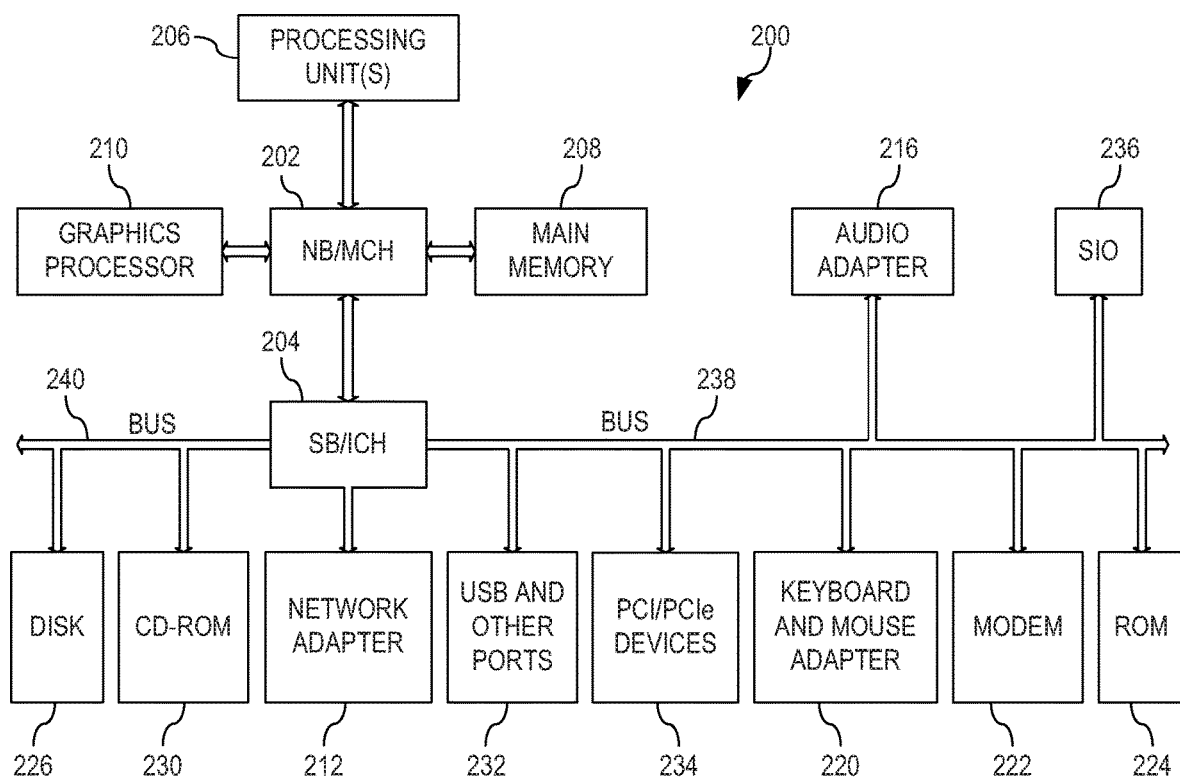
FIG. 2 is a block diagram of an example data processing system in which aspects of the illustrative embodiments are implemented.
Figure 3:
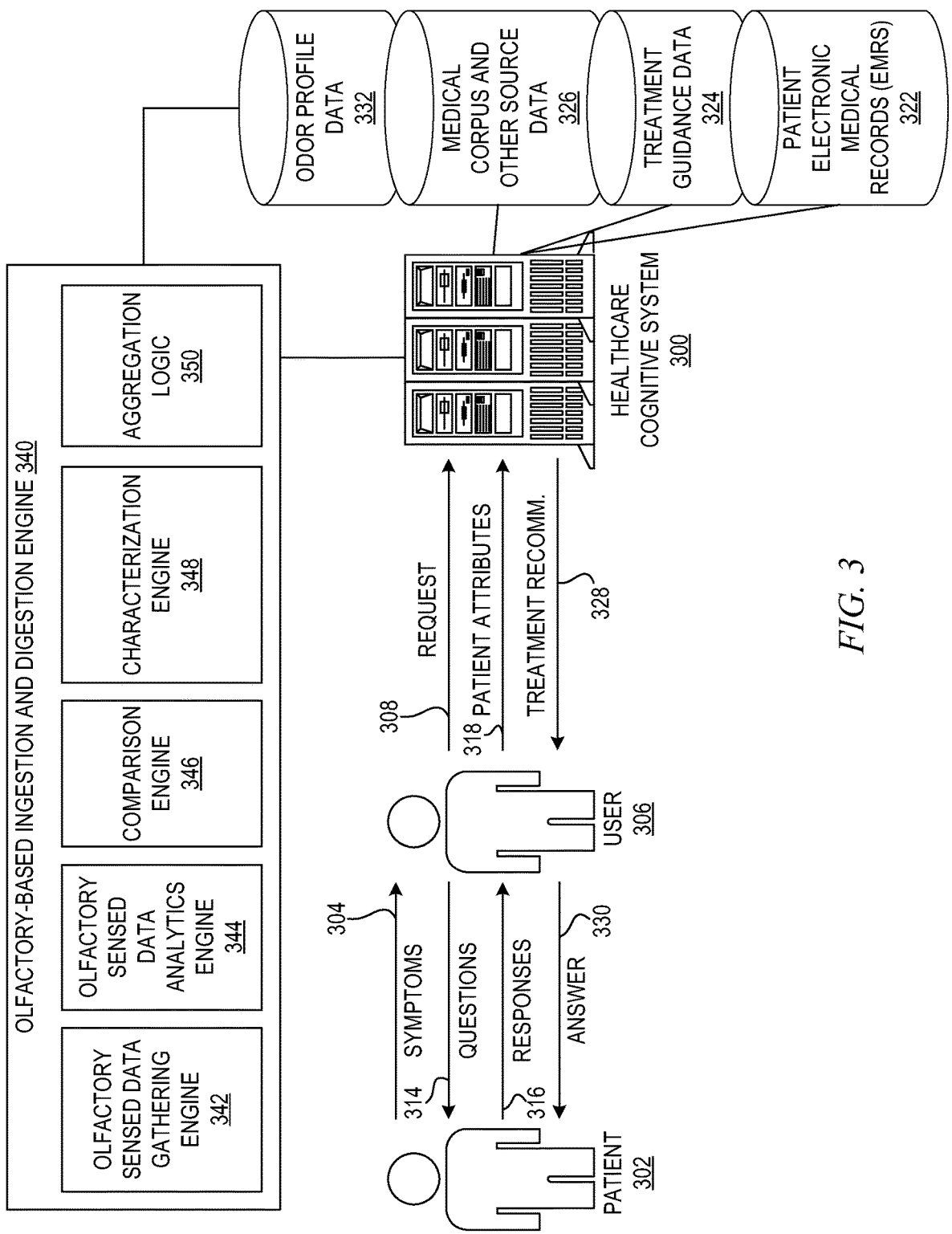
FIG. 3 is an example diagram illustrating an interaction of elements of a olfactory-based cognitive system within a healthcare environment in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for cognitive diagnostics using characterized olfactory-sensed data which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the cognitive system. As described in more detail hereafter, the particular application that is implemented in the cognitive system of the present invention is an application for medical malady diagnosis using characterized olfactory-sensed data.

It should be appreciated that the cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to patient diagnostics using characterized olfactory-sensed data. In other cases, for example, the request processing pipelines may be configured to provide different types of cognitive functions or support different types of applications, such as one request processing pipeline being used for diagnosing automotive issues, identifying chemicals associated with liquids packed in luggage, etc.

Moreover, each request processing pipeline may have its own associated corpus or corpora that they ingest and operate on, e.g., one corpus for medial malady domain related documents, another corpus for automotive issue domain related documents, and another corpus for chemicals associated with liquids packed in luggage domain related documents, in the above examples. In some cases, the request processing pipelines may each operate on the same domain of input questions but may have different configurations, e.g., different annotators or differently trained annotators, such that different analysis and potential answers are generated. The cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P using the provided olfactory-sensed data X identified from olfactometer Y" or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a cognitive system with regard cognitive diagnostics using characterized olfactory-sensed data. That is, for each sensed odor in a plurality of sensed odors sensed by a plurality of electronic noses and olfactometers, characterized olfactory-sensed data is integrated into the corpus of the QA system and the data with which the characterized olfactory-sensed data is associated is augmented to improve the accuracy of diagnostics provide by the QA system. Then, when a question is submitted to the QA system, the functionality of the QA system is extended by utilizing the characterized olfactory-sensed data to improve the accuracy of diagnostics provide by the QA system in providing a set of answers to the question.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding,
  Ingest and process vast amounts of structured and unstructured data,
  Generate and evaluate hypothesis,
  Weigh and evaluate responses that are based only on relevant evidence,
  Provide situation-specific advice, insights, and guidance,
  Improve knowledge and learn with each iteration and interaction through machine learning processes,
  Enable decision making at the point of impact (contextual guidance),
  Scale in proportion to the task,
  Extend and magnify human expertise and cognition,
  Identify resonating, human-like attributes and traits from natural language,
  Deduce various language specific or agnostic attributes from natural language,
  High degree of relevant recollection from data points (images, text, voice) (memorization and recall),
  Predict and sense with situational awareness that mimic human cognition based on experiences, and
  Answer questions based on natural language and specific evidence.

In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, candidate answers, or candidate treatment recommendations to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104, 105, 110, and 112 (comprising one or more processors and one or more memories, and potentially any other computing device elements generally known in the art including buses, storage devices, communication interfaces, and the like) connected to the computer network 102. The network 102 includes multiple computing devices 104, 105, 110, and 112 in communication with each other and with other devices or components via one or more wired and/or wireless data communication links, where each communication link comprises one or more of wires, routers, switches, transmitters, receivers, or the like. The cognitive system 100, which may be implemented in a server computing device such as server 105, and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104, 105, 110, and 112 on the network 102 include access points for content creators and cognitive system users. Some of the computing devices 104, 105, 110, and 112 include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that, the cognitive system 100 may operate in environments of any size, including local and global, e.g. the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a olfactory-based cognitive system, this analysis may involve processing patient medical records, medical guidance documentation from one or more corpora, and the like, along with olfactory-sensed data to provide a cognitive system that utilizes characterized olfactory-sensed data resulting in an improvement in the accuracy of diagnostics in response to a question.

In the context of the present invention, cognitive system 100 may provide a cognitive functionality for an olfactory-based cognitive system with regard cognitive diagnostics using characterized olfactory-sensed data. For example, depending upon the particular implementation, the olfactory-based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a olfactory-based cognitive system 100 that operates in, for example, a medical or healthcare type domain, an automotive domain, a security domain, or the like, and which may process requests for such olfactory-based operations via the request processing pipeline 108 input as either structured or unstructured requests, natural language input questions, or the like. In one illustrative embodiment, the cognitive system 100 is a medical diagnostics and treatment recommendation system that analyzes a patient's symptoms as well as olfactory-sensed data in relation to medical guidelines and other medical documentation in a corpus of information to generate a recommendation as to what medical malady or condition the patient may have as well as how to treat a medical malady or condition of the patient.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing olfactory-based ingestion and digestion engine 120 in order to provide an olfactory-based cognitive diagnosis system. That is, olfactory-based ingestion and digestion engine 120 provides the logic for integrating olfactory-sensed data associated with one or more identified odors such that, when that the olfactory-sensed data is ingested and digested into corpus 106 and 140 to coincide with other data in corpus 106 and 140 of cognitive system 100, olfactory-based diagnoses may be provided QA logic of cognitive system 100 (which is further described hereafter) is implemented for analyzing natural language questions that include olfactory data, identifying candidate answers to those natural language questions using the olfactory data, scoring the candidate answers, and/or selecting a set of one or more final answers for return to an originator of a natural language question as the answers) to the natural language question that takes into consideration the olfactory data.

As shown in FIG. 1, olfactory-based ingestion and digestion engine 120 comprises olfactory-sensed data gathering engine 122, olfactory-sensed data analytics engine 124, comparison engine 126, characterization engine 128, and aggregation logic 130. In order to train cognitive system 100 so that any electronic nose or olfactometer may be utilized to sense an odor and so that cognitive system 100 is able to provide a diagnosis of a malady when input is provided that includes olfactory-sensed data and an identification of the electronic nose or olfactometer utilized to generate the olfactory-sensed data, olfactory-sensed data gathering engine 122 initially gathers olfactory-sensed data for known maladies that that are identifiable using olfactory-sensed data in addition to other input data.

That is, for a particular known malady that may be identified using olfactory-sensed data in addition to other input data, olfactory-based ingestion and digestion engine 120 trains cognitive system 100 so that olfactory-sensed data from a plurality of electronic noses and olfactometers is gathered, analyzed, and associated with the known malady for use in later diagnostics. Thus, for each of a plurality of known maladies that may be identified using olfactory-sensed data, as each of the plurality of electronic noses and olfactometers generates olfactory-sensed data associated with the known malady, olfactory-sensed data gathering engine 122 gathers the olfactory-sensed data. Olfactory-sensed data gathering engine 122 then generates an uncharacterized odor profile and stores the uncharacterized odor profile as being associated with the known malady in corpus 106 and 140 for later analysis.

Using the uncharacterized odor profile for the particular electronic nose or olfactometer and for the known malady, olfactory-sensed data analytics engine 124 analyzes the olfactory-sensory data in the uncharacterized odor profile and, from the multiple variables within the olfactory-sensed data, generates composite scores to form reliable and valid measures of latent, theoretical constructs. The composite scoring model may be compiled specifically for each olfactory test to accommodate the most current understanding of the reliability and sensitivity of the instrumentation, testing equipment, protocol, or the like, relative to a target of the analysis. For example if Test A is currently considered more accurate than Test B for detecting the presence of disease C, then Test A would receive the higher weight. Below a certain sensitivity level, some test results may not make a minimum threshold and therefore should not be used. That distinction may be made by the subject matter experts in the field. For example, some olfactory detection may be in the early stages of development and have a lower threshold, whereas, in other olfactory detection that re more established, there would be a much higher threshold.

Comparison engine 126 then compares the composite scoring associated with the uncharacterized odor profile for the particular electronic nose or olfactometer and for the known malady to actual olfactory-sensory data that has been verified as indicating the known malady. By performing the comparison, comparison engine 126 generates a range of values for the particular electronic nose or olfactometer to the known malady so that, in subsequent cognitive analysis, when the particular odor is sensed by the particular electronic nose or olfactometer, cognitive system 100 can relate the olfactory-sensed data associated with the particular odor to the known malady. Utilizing the generated range of values, characterization engine 128 characterizes the olfactory-sensed data to generate a characterized odor profile. Aggregation logic 130 then aggregates the characterized odor profile into corpus 106 and 140 as being associated with the known malady. Olfactory-based ingestion and digestion engine 120 iteratively repeats the process for each of a plurality of known maladies that may be identified using olfactory-sensed data and for each of the plurality of electronic noses and olfactometers, thereby training cognitive system 100 to diagnose a malady when input is provided that includes olfactory-sensed data and an identification of the electronic nose or olfactometer utilized to generate the olfactory-sensed data.

The resulting additions of the characterized odor profiles to corpus 106 and 140 are then used by cognitive system 100 to analyze input questions/requests, generate candidate answers/results for the input questions/requests, score the candidate answers/results, and/or select one or more final answers/results to be returned to an originator of the input question/request, e.g., a user of client computing device 110 or 112.

As is evident from the above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a olfactory-based cognitive system within a healthcare environment in accordance with one illustrative embodiment. The example diagram of FIG. 3 depicts an implementation of an olfactory-based cognitive system 300 that is configured to provide medical treatment recommendations for patients. However, it should be appreciated that this is only an example implementation and other operations may be implemented in other embodiments of olfactory-based cognitive system 300 without departing from the spirit and scope of the present invention.

Moreover, it should be appreciated that while FIG. 3 depicts patient 302 and user 306 as human figures, the interactions with and between these entities may be performed using computing devices, medical equipment, and/or the like, such that entities 302 and 306 may in fact be computing devices, e.g., client computing devices. For example, interactions 304, 314, 316, and 330 between patient 302 and user 306 may be performed orally, e.g., a doctor interviewing a patient, and may involve the use of one or more medical instruments, monitoring devices, or the like (such as the aforementioned electronic noses and olfactometers), to collect information that may be input to the olfactory-based cognitive system 300 as patient attributes 318. Interactions between user 306 and olfactory-based cognitive system 300 will be electronic via a user computing device (not shown), such as a client computing device 110 or 112 in FIG. 1, communicating with olfactory-based cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. User 306 may interact with patient 302 via a question 314 and response 316 exchange where user 306 gathers more information about patient 302, symptoms 304, and the medical malady or condition of patient 302. It should be appreciated that the questions/responses may in fact also represent user 306 gathering information from patient 302 using various medical equipment, e.g., blood pressure monitors, thermometers, wearable health and activity monitoring devices associated with patient 302 such as a FitBit™, a wearable heart monitor, an electronic nose, an olfactometer, or any other medical equipment that may monitor one or more medical characteristics of patient 302. In some cases such medical equipment may be medical equipment typically used in hospitals or medical centers to monitor vital signs and medical conditions of patients that are present in hospital beds for observation or medical treatment.

In response, user 306 submits request 308 to olfactory-based cognitive system 300, such as via a user interface on a client computing device that is configured to allow users to submit requests to olfactory-based cognitive system 300 in a format that olfactory-based cognitive system 300 is able to parse and process. Request 308 may include, or be accompanied with, information identifying patient attributes 318. These patient attributes 318 may include, for example, an identifier of patient 302 from which patient EMRs 322 for patient 302 may be retrieved, demographic information about patient 302, symptoms 304, and other pertinent information obtained from responses 316 to questions 314 or information obtained from medical equipment used to monitor or gather data about the condition of patient 302, including olfactory-sensed data and an identification of the olfactometer or electronic nose utilized to gather the olfactory-sensed data. Any information about patient 302 that may be relevant to a cognitive evaluation of patient 302 by olfactory-based cognitive system 300 may be included in request 308 and/or patient attributes 318.

Olfactory-based cognitive system 300 provides a cognitive system that is specifically configured to perform an implementation specific healthcare oriented cognitive operation. In the depicted example, this olfactory-based oriented cognitive operation is directed to providing a treatment recommendation 328 to user 306 to assist user 306 in treating patient 302 based on their reported symptoms 304 and other information gathered about patient 302 via question 314 and response 316 process and/or medical equipment monitoring/data gathering. Olfactory-based cognitive system 300 operates on request 308 and patient attributes 318 utilizing information gathered from odor profile data 332, medical corpus and other source data 326, treatment guidance data 324, and patient EMRs 322 associated with the patient 302 to generate one or more treatment recommendation 328. Treatment recommendations 328 may be presented in a ranked ordering with associated supporting evidence, obtained from the patient attributes 318 and data sources 322, 324, 326, and 332, indicating the reasoning as to why the treatment recommendation 328 is being provided and why it is ranked in the manner that it is ranked.

For example, based on request 308 and patient attributes 318, olfactory-based cognitive system 300 may operate on the request, such as by using a QA pipeline type processing as described herein, to parse request 308 and patient attributes 318 to determine what is being requested and the criteria upon which the request is to be generated as identified by patient attributes 318, and may perform various operations for generating queries that are sent to the data sources 322, 324, 326, and 332 to retrieve data, generate candidate treatment recommendations (or answers to the input question), and score these candidate treatment recommendations based on supporting evidence found in the data sources 322, 324, 326, and 332. In the depicted example, patient EMRs 322 is a patient information repository that collects patient data from a variety of sources, e.g., hospitals, laboratories, physicians' offices, health insurance companies, pharmacies, etc. Patient EMRs 322 store various information about individual patients, such as patient 302, in a manner (structured, unstructured, or a mix of structured and unstructured formats) that the information may be retrieved and processed by olfactory-based cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by olfactory-based cognitive system 300 and searched/processed to generate treatment recommendations 328.

Treatment guidance data 324 provides a knowledge base of medical knowledge that is used to identify potential treatments for a patient based on patient's attributes 318 and historical information presented in patient's EMRs 322. Treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that patient 302 is less than or equal to 60 years of age, has acute myeloid leukemia (AML), and no evidence of cardiac disease. Thus, for a patient 402 that is 59 years of age, has AML, and does not have any evidence in their patient attributes 418 or patient EMRs 322 indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment recommendation for consideration for this patient 302. However, if the patient had been 69 years old, the first criterion would not have been met and the Decitabine treatment would not be a candidate treatment recommendation for consideration for this patient 302. Various potential treatment recommendations may be evaluated by olfactory-based cognitive system 300 based on ingested treatment guidance data 324 to identify subsets of candidate treatment recommendations for further consideration by olfactory-based cognitive system 300 by scoring such candidate treatment recommendations based on evidential data obtained from patient EMRs 322 and medical corpus and other source data 326.

For example, data mining processes may be employed to mine the data in sources 322, 326, and 332 to identify evidential data supporting and/or refuting the applicability of the candidate treatment recommendations to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." Olfactory-based cognitive system 300 processes the evidence in accordance with various cognitive logic algorithms to generate a confidence score for each candidate treatment recommendation indicating a confidence that the corresponding candidate treatment recommendation is valid for patient 302. The candidate treatment recommendations may then be ranked according to their confidence scores and presented to user 306 as a ranked listing of treatment recommendations 328. In some cases, only a highest ranked, or final answer, is returned as treatment recommendation 328. Treatment recommendation 328 may be presented to user 306 in a manner that the underlying evidence evaluated by olfactory-based cognitive system 300 may be accessible, such as via a drilldown interface, so that user 306 may identify the reasons why treatment recommendation 328 is being provided by olfactory-based cognitive system 300.

In accordance with the illustrative embodiments herein, olfactory-based cognitive system 300 is augmented to include characterized odor profiles generated by olfactory-based ingestion and digestion engine 340. Olfactory-based ingestion and digestion engine 340 comprises logic elements 342-350 which operate in a similar manner as previously described above with regard to corresponding elements 122-130 in FIG. 1. That is, olfactory-sensed data gathering engine 342 initially gathers olfactory-sensed data for known maladies that that are identifiable using olfactory-sensed data in addition to other input data, generates an uncharacterized odor profile; and stores the uncharacterized odor profile as being associated with the known malady in odor profile data 332. Using the uncharacterized odor profile for the particular electronic nose or olfactometer and for the known malady, olfactory-sensed data analytics engine 344 analyzes the olfactory-sensory data in the uncharacterized odor profile and, from the multiple variables within the olfactory-sensed data, generates composite scores to form reliable and valid measures of latent, theoretical constructs. The composite scoring model may be compiled specifically for each olfactory test to accommodate the most current understanding of the reliability and sensitivity of the instrumentation, testing equipment, protocol, or the like, relative to a target of the analysis. For example if Test A is currently considered more accurate than Test B for detecting the presence of disease C, then Test A would receive the higher weight. Below a certain sensitivity level, some test results may not make a minimum threshold and therefore should not be used. That distinction may be made by the subject matter experts in the field. For example, some olfactory detection may be in the early stages of development and have a lower threshold, whereas, in other olfactory detection that re more established, there would be a much higher threshold.

Comparison engine 346 compares the composite scoring associated with the uncharacterized odor profile for the particular electronic nose or olfactometer and for the known malady to actual olfactory-sensory data that has been verified as indicating the known malady. By performing the comparison, comparison engine 346 generates a range of values for the particular electronic nose or olfactometer to the known malady. Utilizing the generated range of values, characterization engine 348 characterizes the olfactory-sensed data to generate a characterized odor profile. Aggregation logic 350 then aggregates the characterized odor profile into odor profile data 332 as being associated with the known malady.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "What is the appropriate treatment for patient P?" taking into consideration olfactory-sensed data X identified from olfactometer Y, or a request, such as "Diagnose and provide a treatment recommendation for patient P" taking into consideration olfactory-sensed data X identified from olfactometer Y.

Thus, the illustrative embodiments provide mechanisms for improving the diagnostics provide by a olfactory-based cognitive system using olfactory-sensed data. The olfactory-based cognitive system is train the olfactory-based cognitive system for a plurality of odors sensed by a plurality of electronic noses and olfactometers resulting in a plurality of characterized odor profiles each associated with a particular malady. Then, with the characterized olfactory-sensed data being available within the corpus, when a question is submitted to the cognitive system, the cognitive system utilized the characterized olfactory-sensed data to improve the accuracy of diagnostics provide by the cognitive system in providing a set of answers to the question.

Figure 4:
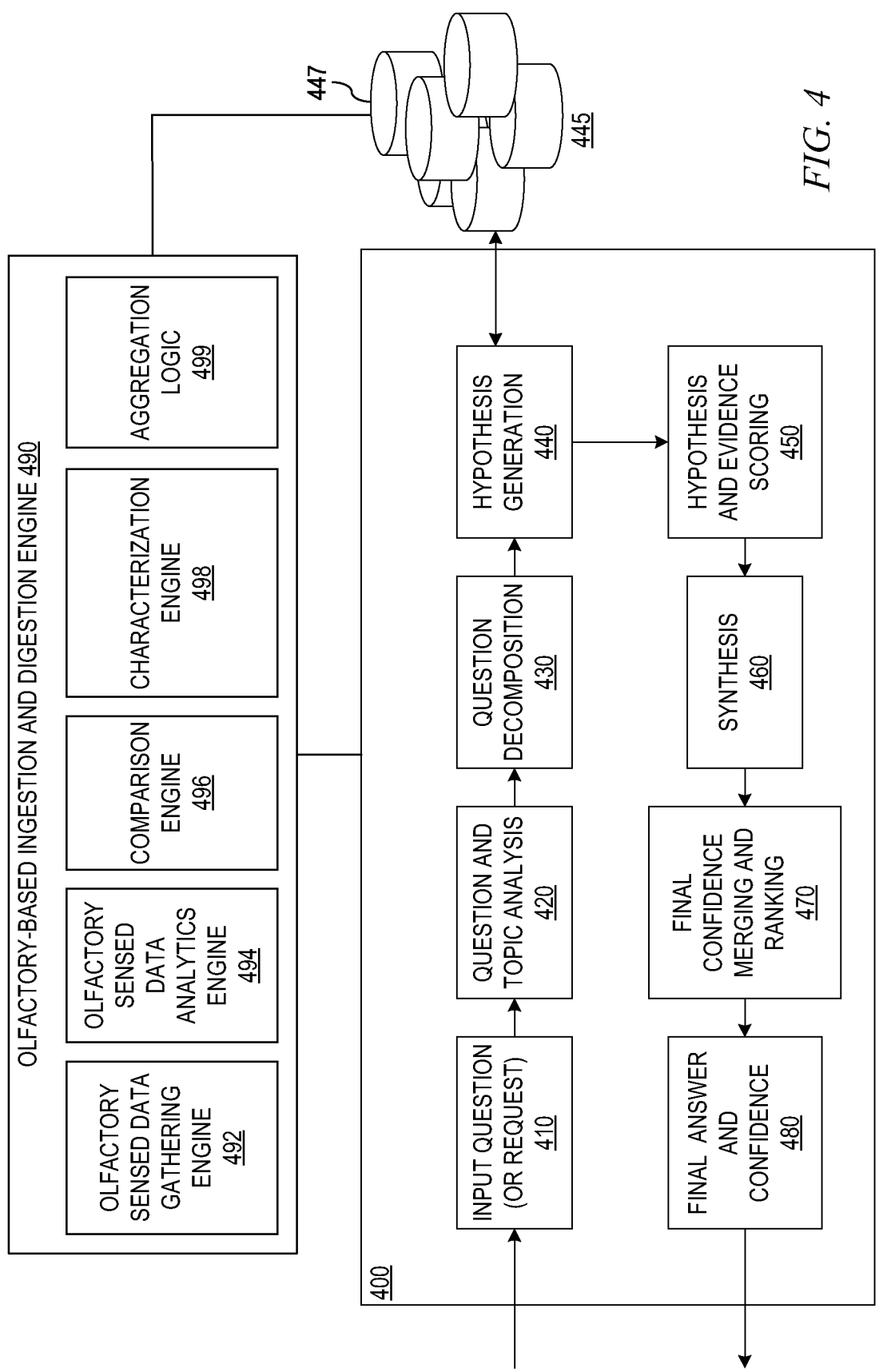
FIG. 4 illustrates a cognitive system processing pipeline for processing a natural language input to generate a response or result in accordance with one illustrative embodiment.

FIG. 4 illustrates an example of a cognitive system processing pipeline which, in the depicted example, is a question and answer (QA) system pipeline used to process an input question in accordance with one illustrative embodiment. As noted above, the cognitive systems with which the illustrative embodiments may be utilized are not limited to QA systems and thus, not limited to the use of a QA system pipeline. FIG. 4 is provided only as one example of the processing structure that may be implemented to process a natural language input requesting the operation of an olfactory-based cognitive system to present a response or result to the natural language input.

The QA system pipeline of FIG. 4 may be implemented, for example, as QA pipeline 108 of cognitive system 100 in FIG. 1. It should be appreciated that the stages of the QA pipeline shown in FIG. 4 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA pipeline of FIG. 4 is augmented, for example, in one or more of the stages to implement the improved mechanism of the illustrative embodiments described hereafter, additional stages may be provided to implement the improved mechanism, or separate logic from the pipeline 400 may be provided for interfacing with the pipeline 400 and implementing the improved functionality and operations of the illustrative embodiments.

As shown in FIG. 4, the QA pipeline 400 comprises a plurality of stages 410-480 through which the cognitive system operates to analyze an input question and generate a final response. In an initial question input stage 410, the QA pipeline 400 receives an input question that is presented in a natural language format as well as olfactory-sensed data identified from an olfactometer and an identification of the olfactometer utilized to sense the olfactory-sensed data. That is, a user inputs, via a user interface, an input question for which the user wishes to obtain an answer, e.g., "What is the appropriate treatment for patient P?" taking into consideration olfactory-sensed data X identified from olfactometer Y, or a request, such as "Diagnose and provide a treatment recommendation for patient P" taking into consideration olfactory-sensed data X identified from olfactometer Y. In response to receiving the input question, the next stage of the QA pipeline 400, i.e. the question and topic analysis stage 420, parses the input question using natural language processing (NLP) techniques to extract major features from the input question, and classify the major features according to types, e.g., names, dates, or any of a plethora of other defined topics.

In addition, the extracted major features include key words and phrases classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 4, the identified major features are then used during the question decomposition stage 430 to decompose the question into one or more queries that are applied to the corpora of data/information 445 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 445. That is, these various sources themselves, different collections of sources, and the like, represent a different corpus 447 within the corpora 445. There may be different corpora 447 defined for different collections of documents based on various criteria depending upon the particular implementation. For example, different corpora may be established for different topics, subject matter categories, sources of information, or the like. As one example, a first corpus may be associated with healthcare documents while a second corpus may be associated with automotive documents. Alternatively, one corpus may be documents published by the U.S. Department of Energy while another corpus may be IBM Redbooks documents. Any collection of content having some similar attribute may be considered to be a corpus 447 within the corpora 445.

The queries are applied to one or more databases storing information about the electronic texts, documents, articles, websites, and the like, that make up the corpus of data/information, e.g., the corpus of data 106 and 140 in FIG. 1. Again, in accordance with the illustrative embodiments, one or more corpus 447 within corpora 445 is augmented to include characterized odor profiles generated by olfactory-based ingestion and digestion engine 490. Olfactory-based ingestion and digestion engine 490 comprises logic elements 492-499 which operate in a similar manner as previously described above with regard to corresponding elements 342-350 of FIG. 3 and corresponding elements 122-130 in FIG. 1. That is, olfactory-sensed data gathering engine 492 initially gathers olfactory-sensed data for known maladies that that are identifiable using olfactory-sensed data in addition to other input data, generates an uncharacterized odor profile, and stores the uncharacterized odor profile as being associated with the known malady in one of corpus 447. Using the uncharacterized odor profile for the particular electronic nose or olfactometer and for the known malady, olfactory-sensed data analytics engine 494 analyzes the olfactory-sensory data in the uncharacterized odor profile and, from the multiple variables within the olfactory-sensed data, generates composite scores to form reliable and valid measures of latent, theoretical constructs. The composite scoring model may be compiled specifically for each olfactory test to accommodate the most current understanding of the reliability and sensitivity of the instrumentation, testing equipment, protocol, or the like, relative to a target of the analysis. For example if Test A is currently considered more accurate than Test B for detecting the presence of disease C, then Test A would receive the higher weight. Below a certain sensitivity level, some test results may not make a minimum threshold and therefore should not be used. That distinction may be made by the subject matter experts in the field. For example, some olfactory detection may be in the early stages of development and have a lower threshold, whereas, in other olfactory detection that re more established, there would be a much higher threshold.

Comparison engine 496 compares the composite scoring associated with the uncharacterized odor profile for the particular electronic nose or olfactometer and for the known malady to actual olfactory-sensory data that has been verified as indicating the known malady. By performing the comparison, comparison engine 496 generates a range of values for the particular electronic nose or olfactometer to the known malady. Utilizing the generated range of values, characterization engine 498 characterizes the olfactory-sensed data to generate a characterized odor profile. Aggregation logic 499 then aggregates the characterized odor profile into corpus 447 as being associated with the known malady.

Therefore, queries are applied to the corpus of data/information at the hypothesis generation stage 440 to generate results identifying potential hypotheses for answering the input question, which can then be evaluated. That is, the application of the queries results in the extraction of portions of the corpus of data/information matching the criteria of the particular query, which in accordance with the illustrative embodiments include characterized olfactory-sensed data correlated to the olfactometer or electronic nosed that provided the olfactory-sensed data on which the characterized olfactory-sensed data is based. These portions of the corpus are then analyzed and used, during the hypothesis generation stage 440, to generate hypotheses for answering the input question. These hypotheses are also referred to herein as "candidate answers" or "candidate treatment recommendations" for the input question. For any input question, at this stage 440, there may be hundreds of hypotheses, candidate answers, or candidate answers generated that may need to be evaluated.

The QA pipeline 400, in stage 450, then performs a deep analysis and comparison of the language of the input question and the language of each hypothesis, candidate answer, or candidate treatment recommendations as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis, candidate answer, candidate treatment recommendations, to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that, this is just one simple example of how scoring can be performed. Many other algorithms of various complexities may be used to generate scores for candidate answers and evidence without departing from the spirit and scope of the present invention.

In the synthesis stage 460, the large number of scores generated by the various reasoning algorithms is synthesized into confidence scores or confidence measures for the various hypotheses. This process involves applying weights to the various scores, where the weights have been determined through training of the statistical model employed by the QA pipeline 400 and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 400 that identifies a manner by which these scores may be combined to generate a confidence score or measure for the individual hypotheses or candidate answers. This confidence score or measure summarizes the level of confidence that the QA pipeline 400 has about the evidence that the candidate answer is inferred by the input question, i.e. that the candidate answer is the correct answer for the input question.

The resulting confidence scores or measures are processed by a final confidence merging and ranking stage 470 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 480, a final answer and confidence score, or final set of candidate answers and confidence scores, are generated and output to the submitter of the original input question via a graphical user interface or other mechanism for outputting information.

The present invention may be a system, a method, and/or a computer program product. The computer program product may include a computer readable storage medium (or media) having computer readable program instructions thereon for causing a processor to catty out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 5:
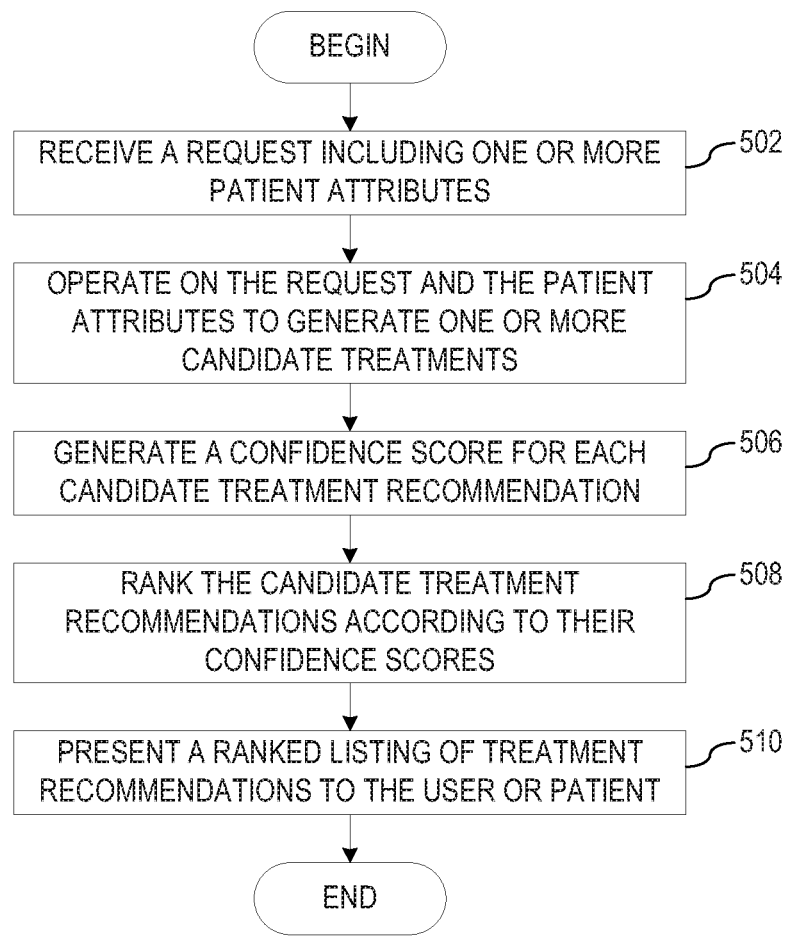
FIG. 5 depicts an exemplary flowchart of the operation performed by an olfactory-based cognitive system in responding to a question or request that includes olfactory-sensed data and an identification of a device that generated the olfactory-sensed data in accordance with an illustrative embodiment.

FIG. 5 depicts an exemplary flowchart of the operation performed by an olfactory-based cognitive system in responding to a question or request that includes olfactory-sensed data and an identification of a device that generated the olfactory-sensed data in accordance with an illustrative embodiment. As the operation begins, the olfactory-based cognitive system receives a request from a patient or user, the request including one or more patient attributes (step 502), such as, for example, an identifier of the patient from which patient electronic medical records (EMRs) for the patient may be retrieved, demographic information about the patient, symptoms experienced by the patient, other pertinent information obtained from responses to questions, information obtained from medical equipment used to monitor or gather data about the condition of the patient, including olfactory-sensed data and an identification of the olfactometer or electronic nose utilized to gather the olfactory-sensed data. That is, any information about the patient that may be relevant to a cognitive evaluation of the patient by the olfactory-based cognitive system may be included in the request and/or the patient attributes.

The olfactory-based cognitive system operates on the request and the patient attributes utilizing information gathered from data sources such as odor profile data, medical corpus and other source data, treatment guidance data, and patient EMRs associated with the patient to generate one or more candidate treatment recommendations (step 504). In accordance with various cognitive logic algorithms, the olfactory-based cognitive system generates a confidence score for each candidate treatment recommendation indicating a confidence that the corresponding candidate treatment recommendation is valid for the patient (step 506). The olfactory-based cognitive system then ranks the candidate treatment recommendations according to their confidence scores (step 508) and presents a ranked listing of treatment recommendations to the user or patient (step 510), with the operation ending thereafter.

Figure 6:
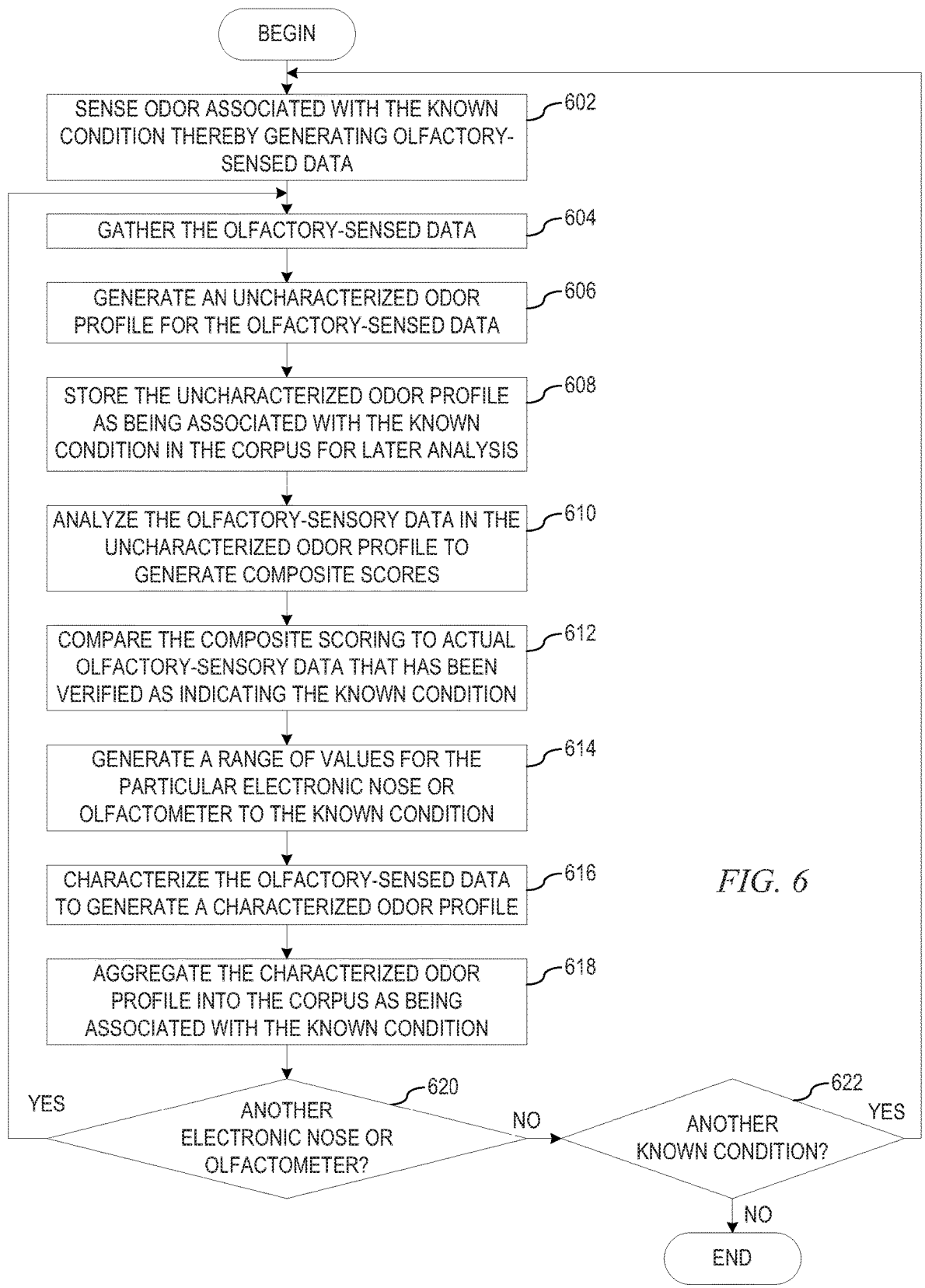
FIG. 6 depicts an exemplary flowchart of the operation performed by an olfactory-based ingestion and digestion engine in ingesting and digesting olfactory-sensed data into a corpus of an olfactory-based cognitive system in accordance with an illustrative embodiment.

FIG. 6 depicts an exemplary flowchart of the operation performed by an olfactory-based ingestion and digestion engine in ingesting and digesting olfactory-sensed data into a corpus of an olfactory-based cognitive system in accordance with an illustrative embodiment. As the operation begins, for each of a set of known conditions that may be identified using olfactory-sensed data, a plurality of electronic noses and olfactometers each sense the odor associated with the known condition thereby generating olfactory-sensed data (step 602). As each of the plurality of electronic noses and olfactometers generates the olfactory-sensed data associated with the known condition, the olfactory-based ingestion and digestion engine gathers the olfactory-sensed data (step 604). The olfactory-based ingestion and digestion engine generates an uncharacterized odor profile for the olfactory-sensed data (step 606) and stores the uncharacterized odor profile as being associated with the known condition in the corpus for later analysis (step 608).

Using the uncharacterized odor profile for the particular electronic nose or olfactometer and for the known condition, the olfactory-based ingestion and digestion engine analyzes the olfactory-sensory data in the uncharacterized odor profile and, from the multiple variables within the olfactory-sensed data, generates composite scores to form reliable and valid measures of latent, theoretical constructs (step 610). The composite scoring model may be compiled specifically for each olfactory test to accommodate the most current understanding of the reliability and sensitivity of the instrumentation, testing equipment, protocol, or the like, relative to a target of the analysis. For example if Test A is currently considered more accurate than Test B for detecting the presence of disease C, then Test A would receive the higher weight. Below a certain sensitivity level, some test results may not make a minimum threshold and therefore should not be used. That distinction may be made by the subject matter experts in the field. For example, some olfactory detection may be in the early stages of development and have a lower threshold, whereas, in other olfactory detection that re more established, there would be a much higher threshold.

The olfactory-based ingestion and digestion engine compares the composite scoring associated with the uncharacterized odor profile for the particular electronic nose or olfactometer and for the known condition to actual olfactory-sensory data that has been verified as indicating the known condition (step 612). By performing the comparison, the olfactory-based ingestion and digestion engine generates a range of values for the particular electronic nose or olfactometer to the known condition (step 614). This operation is performed so that, in subsequent cognitive analysis, when the particular odor is sensed by the particular electronic nose or olfactometer, the olfactory-based cognitive system may relate the olfactory-sensed data associated with the particular odor to the known malady.

Utilizing the generated range of values, the olfactory-based ingestion and digestion engine characterizes the olfactory-sensed data to generate a characterized odor profile (step 616). The olfactory-based ingestion and digestion engine then aggregates the characterized odor profile into the corpus as being associated with the known condition (step 618). The olfactory-based ingestion and digestion engine then determines whether there is another electronic nose or olfactometer in the plurality of electronic noses and olfactometers for which to process olfactory-sensed data for the current known condition (step 620). If at step 620 there is another electronic nose or olfactometer for which to process olfactory-sensed data for the current known condition, the operation returns to step 604. If at step 620 there is no other electronic nose or olfactometer for which to process olfactory-sensed data for the current known condition, the olfactory-based ingestion and digestion engine determines whether there is another condition in the set of known conditions to process (step 622). If at step 622 there is another known condition, the operation returns to step 602. If at step 622 there is no other known condition to process, the operation terminates.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for improving the diagnostics provide by a olfactory-based cognitive system using olfactory-sensed data, The olfactory-based cognitive system is train the olfactory-based cognitive system for a plurality of odors sensed by a plurality of electronic noses and olfactometers resulting in a plurality of characterized odor profiles each associated with a particular malady. Then, with the characterized olfactory-sensed data being available within the corpus. When a question is submitted to the cognitive system, the cognitive system utilized the characterized olfactory-sensed data to improve the accuracy of diagnostics provide by the cognitive system in providing a set of answers to the question.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement an olfactory-based cognitive diagnosis system, wherein the data processing system operates to:

train the olfactory-based cognitive diagnosis system using known olfactory-sensed data and a plurality of electronic noses and olfactometers that sensed the known olfactory-sensed data to provide a cognitive diagnosis by:

for each known malady of a set of known maladies:

gathering known olfactory-sensed data associated with the known malady from a set of known olfactory-sensed data, wherein each known olfactory-sensed data identifies an olfactometer or an electronic nose from the plurality of electronic noses and olfactometers that sensed the known olfactory-sensed data;

generating an uncharacterized odor profile for the known olfactory-sensed data;

analyzing the known olfactory-sensory data in the uncharacterized odor profile for the known olfactory-sensed data to generate composite scores for the known olfactory-sensed data;

comparing the generated composite scores fix the known olfactory-sensed data to actual olfactory-sensory data that has been verified as indicating the known malady;

generating a range of values for the electronic nose or olfactometer associated with the known olfactory-sensory data;

characterizing input olfactory-sensed data by utilizing the generated range of values to generate a characterized odor profile for the known olfactory-sensed data; and aggregating the characterized odor profile into the odor profile data as being associated with the known malady;

sense olfactory-sensed data using one of the plurality of electronic noses and olfactometers, thereby forming sensed olfactory data;

parse an input request from a user for a diagnosis of a malady using natural language processing to extract one or more attributes from data sources, wherein the one or more attributes include at least the sensed olfactory data, an identification of the olfactometer or the electronic nose from the plurality of electronic noses and olfactometers that sensed the sensed olfactory data, and information obtained from patient responses to a set of questions;

generate a set of candidate recommendations for the diagnosis of the malady utilizing the one or more attributes, wherein each candidate recommendation in the set of candidate recommendations is generated from odor profile data using the sensed olfactory data, the identification of the olfactometer or the electronic nose that sensed the sensed olfactory data, and the information obtained from patient responses to the set of questions;

generate a confidence score for each candidate recommendation in the set of candidate recommendations indicating a confidence that the corresponding candidate recommendation is valid to address the input request;

rank each candidate recommendation in the set of candidate recommendations according to its respective confidence scores; and present a ranked listing of candidate recommendations to the user for use in addressing the input request.

2. The method of claim 1, wherein the attributes further include an identifier of a patient from which patient electronic medical records (EMRs) for the patient are retrieved, demographic information about the patient, symptoms experienced by the patient, and information obtained from medical equipment used to monitor or gather data about the malady of the patient.

3. The method of claim 1, wherein the data sources include one or more of the odor profile data, medical corpus and other source data, treatment guidance data, and patient electronic medical records (EMRs) associated with a patient that is a subject of the input request.

4. The method of claim 1, wherein generating the composite scores utilizes a composite scoring model compiled specifically for each olfactory test to accommodate a current understanding of reliability and sensitivity of the olfactometer or electronic nose relative to the known malady.

5. The method of claim 1, wherein the odor profile data associates the known malady to the olfactory-sensed data for each of the plurality of olfactometers and electronic noses utilized to gather the olfactory-sensed data for use in subsequent cognitive analysis that relates the olfactory-sensed data associated with the particular odor to the known malady.

6. A computer program product comprising a computer readable storage medium having a computer readable program to implement an olfactory-based cognitive diagnosis system stored therein, wherein the computer readable program, when executed on a computing device, causes the computing device to:

train the olfactory-based cognitive diagnosis system using known olfactory-sensed data and a plurality of electronic noses and olfactometers that sensed the known olfactory-sensed data to provide a cognitive diagnosis by:

for each known malady of a set of known maladies:

gathering known olfactory-sensed data associated with the known malady from a set of known olfactory-sensed data, wherein each known olfactory-sensed data identifies an olfactometer or an electronic nose from the plurality of electronic noses and olfactometers that sensed the known olfactory-sensed data;

generating an uncharacterized odor profile for the known olfactory-sensed data;

analyzing the known olfactory-sensory data in the uncharacterized odor profile for the known olfactory-sensed data to generate composite scores for the known olfactory-sensed data;

comparing the generated composite scores for the known olfactory-sensed data to actual olfactory-sensory data that has been verified as indicating the known malady;

generating a range of values for the electronic nose or olfactometer associated with the known olfactory-sensory data;

characterizing input olfactory-sensed data by utilizing the generated range of values to generate a characterized odor profile for the known olfactory-sensed data; and aggregating the characterized odor profile into the odor profile data as being associated with the known malady;

sense olfactory-sensed data using one of the plurality of electronic noses and olfactometers, thereby forming sensed olfactory data;

parse an input request from a user for a diagnosis of a malady using natural language processing to extract one or more attributes from data sources, wherein the one or more attributes include at least the sensed olfactory data, an identification of the olfactometer or the electronic nose from the plurality of electronic noses and olfactometers that sensed the sensed olfactory data, and information obtained from patient responses to a set of questions;

generate a set of candidate recommendations for the diagnosis of the malady utilizing the one or more attributes, wherein each candidate recommendation in the set of candidate recommendations is generated from odor profile data using the sensed olfactory data, the identification of the olfactometer or the electronic nose that sensed the sensed olfactory data, and the information obtained from patient responses to the set of questions;

generate a confidence score for each candidate recommendation in the set of candidate recommendations indicating a confidence that the corresponding candidate recommendation is valid to address the input request;

rank each candidate recommendation in the set of candidate recommendations according to its respective confidence scores; and present a ranked listing of candidate recommendations to the user for use in addressing the input request.

7. The computer program product of claim 6, wherein the attributes further include an identifier of a patient from which patient electronic medical records (EMRs) for the patient are retrieved, demographic information about the patient, symptoms experienced by the patient, and information obtained from medical equipment used to monitor or gather data about the malady of the patient.

8. The computer program product of claim 6, wherein the data sources include one or more of the odor profile data, medical corpus and other source data, treatment guidance data, and patient electronic medical records (EMRs) associated with a patient that is a subject of the input request.

9. The computer program product of claim 6, wherein generating the composite scores utilizes a composite scoring model compiled specifically for each olfactory test to accommodate a current understanding of reliability and sensitivity of the olfactometer or electronic nose relative to the known malady.

10. The computer program product of claim 6, wherein the odor profile data associates the known malady to the olfactory-sensed data for each of the plurality of olfactometers and electronic noses utilized to gather the olfactory-sensed data for use in subsequent cognitive analysis that relates the olfactory-sensed data associated with the particular odor to the known malady.

11. An apparatus for implementing an olfactory-based cognitive system comprising:
a processor; and
a memory coupled to the processor, wherein the memory comprises instructions which, when executed by the processor, cause the processor to:
train the olfactory-based cognitive diagnosis system using known olfactory-sensed data and a plurality of electronic noses and olfactometers that sensed the known olfactory-sensed data to provide a cognitive diagnosis by:
for each known malady of a set of known maladies:
gathering known olfactory-sensed data associated with the known malady from a set of known olfactory-sensed data, wherein each known olfactory-sensed data identifies an olfactometer or an electronic nose from the plurality of electronic noses and olfactometers that sensed the known olfactory-sensed data;
generating an uncharacterized odor profile for the known olfactory-sensed data;
analyzing the known olfactory-sensory data in the uncharacterized odor profile for the known olfactory-sensed data to generate composite scores for the known olfactory-sensed data;
comparing the generated composite scores for the known olfactory-sensed data to actual olfactory-sensory data that has been verified as indicating the known malady;
generating a range of values for the electronic nose or olfactometer associated with the known olfactory-sensory data;
characterizing input olfactory-sensed data by utilizing the generated range of values to generate a characterized odor profile for the known olfactory-sensed data; and
aggregating the characterized odor profile into the odor profile data as being associated with the known malady;
sense olfactory-sensed data using one of the plurality of electronic noses and olfactometers, thereby forming sensed olfactory data;
parse an input request from a user for a diagnosis of a malady using natural language processing to extract one or more attributes from data sources, wherein the one or more attributes include at least the sensed olfactory data, an identification of the olfactometer or the electronic nose from the plurality of electronic noses and olfactometers that sensed the sensed olfactory data, and information obtained from patient responses to a set of questions;
generate a set of candidate recommendations for the diagnosis of the malady utilizing the one or more attributes, wherein each candidate recommendation in the set of candidate recommendations is generated from odor profile data using the sensed olfactory data, the identification of the olfactometer or the electronic nose that sensed the sensed olfactory data, and the information obtained from patient responses to the set of questions;
generate a confidence score for each candidate recommendation in the set of candidate recommendations indicating a confidence that the corresponding candidate recommendation is valid to address the input request;
rank each candidate recommendation in the set of candidate recommendations according to its respective confidence scores; and
present a ranked listing of candidate recommendations to the user for use in addressing the input request.

12. The apparatus of claim 11, wherein the attributes further include an identifier of a patient from which patient electronic medical records (EMRs) for the patient are retrieved, demographic information about the patient, symptoms experienced by the patient, and information obtained from medical equipment used to monitor or gather data about the malady of the patient.

13. The apparatus of claim 11, wherein the data sources include one or more of the odor profile data, medical corpus and other source data, treatment guidance data, and patient electronic medical records (EMRs) associated with a patient that is a subject of the input request.

14. The apparatus of claim 11, wherein generating the composite scores utilizes a composite scoring model compiled specifically for each olfactory test to accommodate a current understanding of reliability and sensitivity of the olfactometer or electronic nose relative to the known malady and wherein the odor profile data associates the known malady to the olfactory-sensed data for each of the plurality of olfactometers and electronic noses utilized to gather the olfactory-sensed data for use in subsequent cognitive analysis that relates the olfactory-sensed data associated with the particular odor to the known malady.

* * * * *